(12) United States Patent
Constantino (10) Patent No.: US 9,622,963 B2
(45) Date of Patent: Apr. 18, 2017

(54) METHODS FOR STIMULATING GROWTH AND PREVENTING LOSS OF HUMAN HAIR

(75) Inventor: Steven Constantino, LaGrange, OH (US)

(73) Assignee: NNC Blending LLC, LaGrange, OH (US)

( * ) Notice: Subject to any disclaimer, the term of this patent is extended or adjusted under 35 U.S.C. 154(b) by 90 days.

(21) Appl. No.: 13/519,972

(22) PCT Filed: Dec. 29, 2010

(86) PCT No.: PCT/US2010/062367
§ 371 (c)(1),
(2), (4) Date: Dec. 4, 2012

(87) PCT Pub. No.: WO2011/082235
PCT Pub. Date: Jul. 7, 2011

(65) Prior Publication Data
US 2013/0078301 A1    Mar. 28, 2013

Related U.S. Application Data

(60) Provisional application No. 61/291,549, filed on Dec. 31, 2009.

(51) Int. Cl.
| | | |
|---|---|---|
| *A61K 8/97* | (2017.01) | |
| *A61K 8/31* | (2006.01) | |
| *A61K 8/34* | (2006.01) | |
| *A61K 8/92* | (2006.01) | |
| *A61Q 5/00* | (2006.01) | |
| *A61Q 7/00* | (2006.01) | |
| *A61K 36/61* | (2006.01) | |
| *A61Q 1/10* | (2006.01) | |
| *A61Q 17/04* | (2006.01) | |
| *A61Q 19/02* | (2006.01) | |

(52) U.S. Cl.
CPC ............... *A61K 8/97* (2013.01); *A61K 8/31* (2013.01); *A61K 8/34* (2013.01); *A61K 8/922* (2013.01); *A61K 36/61* (2013.01); *A61Q 1/10* (2013.01); *A61Q 5/00* (2013.01); *A61Q 7/00* (2013.01); *A61Q 17/04* (2013.01); *A61Q 19/02* (2013.01)

(58) Field of Classification Search
CPC ........... A61Q 17/04; A61Q 19/08; A61Q 5/04
See application file for complete search history.

(56) References Cited

U.S. PATENT DOCUMENTS

| | | | |
|---|---|---|---|
| 7,025,955 B2 | 4/2006 | Siddiqui et al. | |
| 8,470,880 B2 * | 6/2013 | Hu et al. ....................... | 514/557 |
| 2006/0265028 A1 * | 11/2006 | Houle et al. ................... | 607/88 |
| 2007/0154432 A1 | 7/2007 | Davis | |
| 2009/0123564 A1 | 5/2009 | Jain et al. | |
| 2010/0092398 A1 * | 4/2010 | Reynolds ....................... | 424/43 |

FOREIGN PATENT DOCUMENTS

DE    10017865 A1 *  10/2001 ............... A61K 7/06

OTHER PUBLICATIONS

International Search Report; Corresponding PCT Application Serial No. PCT/US2010/062367; filed Dec. 29, 2010; Authorized Officer Choi Sun Hee (4 pages).

P.H. Hart et al., Terpinen-4-ol, the main component of the essential oil of *Melaleuca alternifolia* (tea tree oil), supresses inflammatory mediator production by activated human monocytes. Inflamm. Res., 49: 619-626 (2000) see abstract: p. 619.

* cited by examiner

*Primary Examiner* — Nannette Holloman
(74) *Attorney, Agent, or Firm* — Benesch, Friedlander, Coplan & Aronoff LLP (57) ABSTRACT

A method for stimulating hair growth includes providing a topical composition including a purified oil extract from *Melaleuca alternifolia*, also known as tea tree. The method may further include applying the topical composition to the skin surrounding the follicles of the human hair at least once a day.

A method for preventing the loss of human hair includes providing a topical composition including a purified oil extract from *Melaleuca alternifolia*, also known as tea tree. The method may further include applying the topical composition to the skin surrounding the follicles of the human hair at least once a day.

38 Claims, 10 Drawing Sheets

METHODS FOR STIMULATING GROWTH AND PREVENTING LOSS OF HUMAN HAIR

This application claims priority to PCT Application No. PCT/US10/62367, filed on Dec. 29, 2010, which claims priority to U.S. Provisional Application No. 61/291,549, filed on Dec. 31, 2009.

FIELD OF THE INVENTION

This application relates to methods for stimulating the growth of human hair and to compositions useful in those methods. The application also relates to methods for preventing the loss of human hair and to compositions useful in those methods.

BACKGROUND

Common baldness, also known as alopecia, represents the vast majority of all cases of hair loss in humans. The condition is characterized by the gradual loss of hair mostly in men, but also in women. Most current treatments for common baldness are based on the theory that alopecia originates from genetic factors and aging.

Treatments for common baldness include hair transplantation, oral, and topical application of drugs and natural solutions. Hair transplantation methods are usually painful, costly, and frequently result in an undesirable, unnatural appearance. The predominant oral and topical products are pharmaceuticals such as Rogaine® and Regaine® (topical solutions of the drug minoxidil from Upjohn, Inc.), Propecia® and Proscar® (orally ingested tablet of the drug finasteride from Merck and Company, Inc.), Andolactone® (orally ingested tablets or topical solutions of the drug sprionolactone from G. D. Searle, Inc.), Androcur® (orally ingested tablet of the drugs cyproterone acetate and ethinyl estradiol from Schering-Plough, Inc.), Eulexin® (oral tablets of the drug flutamide from Schering-Plough, Inc.). Additionally, oral contraceptives (containing estrogens and/or estradiol), tretinoin, and azelaic acid are drugs that have been the subject of scientific studies for their potential to enhance hair growth. There are also a variety of other products on the market today that claim to aid in the growth of hair. Some of these treatments may have undesirable side effects or may result in recurrence of the condition if application is discontinued.

Hair grows from follicles in the skin that extend from the epidermis (the outmost layer of skin) to the dermis (the deepest layer of the skin). Hair growth is a complex biochemical process that is only partially understood, in part because it is extremely difficult to isolate single hair follicles and grow them in culture medium. However, it is well recognized that hair grows from active hair follicles at a rate of 0.2 to 0.5 millimeters (0.01 to 0.02 inches) per day. Hair growth is not a continuous phenomenon, but rather occurs in cycles of anagen (active growth), catagen (transition to no growth), and telogen (dormancy). A typical anagen phase lasts for 2 to 10 years, after which the cells at the base of the hair follicle enter catagen for about 14 to 21 days. At the end of the catagen phase, the follicle enters the telogen phase, and becomes dormant for a period of 30 to 90 days. During this phase, the previously growing hair detaches from the base of the follicle, and is eventually shed from the skin as it is pushed out of the follicle by the growth of new hair strand that occurs when the follicle enters a new anagen phase.

SUMMARY

The present exemplary embodiments describe methods for stimulating hair growth and for preventing the loss of human hair and compositions useful in those methods. A method for stimulating hair growth includes providing a topical composition including a purified oil extract from *Melaleuca alternifolia*, also known as tea tree. The method may further include applying the topical composition to the skin surrounding the follicles of the human hair at least once a day. A method for preventing the loss of human hair includes providing a topical composition including a purified oil extract from *Melaleuca alternifolia*, also known as tea tree. The method may further include applying the topical composition to the skin surrounding the follicles of the human hair at least once a day.

DETAILED DESCRIPTION

In the context of this patent application, human hair includes, but is not limited to, head hair, scalp hair, eyelashes, eyebrows, mustaches, beards, chest hair, leg hair, arm hair, and combinations thereof. Human hair may include hair in a male or female of the human species.

Stimulating Hair Growth

An exemplary method for stimulating the growth of human hair is provided. As used herein the term stimulating the growth of human hair means increasing the density of hair (i.e., the number of hairs per $cm^2$ of skin) that is growing in a given area of the human body as compared to the density prior to the use of the method and can also include, either optionally or in addition, increasing the thickness (or cross-sectional area) of existing hair strands. In certain embodiments, the density increases by at least 10% when the method is utilized for at least 8 weeks, at least 14 weeks or at least 18 weeks. In some embodiments, the method results in increases in density of at least 20%, at least 25%, at least 30%, at least 40%, at least 50% or more when utilized for the same time periods. In certain embodiments, the cross-sectional area of existing hair strands increases by at least 10% when the method is utilized for the same time periods. In some embodiments, the method results in increases in the cross-sectional area of at least 20%, at least 25%, at least 30%, at least 40%, at least 50% or more when utilized for the same time periods. Preferably, the thickness of a large percentage (e.g., at least 50% or more) of existing hair strands is increased by the specified amounts, although the methods encompass increases in thickness in other percentages such as at least 10%, at least 20%, at least 30% or more. The exemplary method includes providing a topical composition including a purified oil extract from *Melaleuca alternifolia*, also known as tea tree. The method may further include applying the topical composition to the skin surrounding the follicles of the human hair (or to the skin area that previously surrounded the follicles of the human hair prior to loss of the hair) at least once a day. In one embodiment, applying the topical composition occurs twice a day. In some embodiments, applying the topical composition occurs more frequently, such as three times a day, four times a day or more.

In one embodiment, the exemplary method for stimulating the growth of hair is used for treating hair loss resulting from alopecia and the step of applying the topical composition consists of application to the scalp at areas of thinning or complete hair loss. In one embodiment, the step of applying the topical composition to the skin is done carefully to ensure that the topical composition is substantially applied only to the skin and to avoid applying the topical composition to the hair strands (i.e., more than 95% of the topical composition is applied to the skin or less than 5% of the topical composition has contact with the outer 50% of the length of the hair strands). In some embodiments, the human hair being treated includes eyelashes and the step of applying the topical composition includes application of the topical composition to an area including an eyelid in the immediate vicinity of the normal lash line, eyelashes, and the base of the eyelash.

In one embodiment, application of the topical composition includes rubbing the topical composition into the skin. In some embodiments, the topical composition is rubbed into the skin for from a few seconds to half a minute. In other embodiments, the topical composition is rubbed into the skin for from one half a minute to one minutes. In yet other embodiments, the topical composition is rubbed into the skin for longer than one minute, such as for two minutes. In some embodiments, the topical composition that has been applied to the skin may be allowed to remain on the skin for extended periods of time. In one embodiment, the topical composition may be allowed to remain on the skin after the application for one hour. In one embodiment, the topical composition may be allowed to remain on the skin after the application for two hours. In one embodiment, the topical composition may be allowed to remain on the skin after application for four hours. In one embodiment, the topical composition may be allowed to remain on the skin indefinitely after application. In this embodiment, the topical composition is not removed from the skin such as by wiping, washing or rinsing, but is instead allowed to remain on the skin until it is removed by normal or routine hygiene practices such as shampooing or washing. In certain embodiments, after the topical composition is applied to the skin, heat is applied to the skin such as from a hair dryer or heating pad to aid in absorption of the composition.

In one embodiment, the exemplary method for stimulating the growth of human hair is also effective in bringing back the natural pigmentation of hair. A method is effective in bringing back the natural pigmentation of hair if its usage results in at least 15% of re-growing hair strands growing from the skin to which the composition has been applied having pigmentation (as opposed to lacking pigmentation e.g., by being clear to gray). In other embodiments, relatively more of the hair strands have a return of pigmentation (e.g., 20% or more, 25% or more, or even 50% or more). Preferably, this occurs after the method is utilized for at least 8 weeks, and in some instances at least 14 weeks or at least 18 weeks.

For convenience or efficacy of application, the topical composition may be provided in various forms including, but not limited to, application stick, mascara, eyebrow coloring, lotions, creams, aerosols, sprays, gels, foams, ointments, oils, mousse, emulsions, colloidals, solutions, suspensions, spray-on formulations, brush-on formulations, hair spray, moisturizer, and combinations thereof.

The topical composition may comprise at least 0.02% by weight of the purified oil extract. In one embodiment, the topical composition comprises 0.02% to 25% by weight of the purified oil extract. In some embodiments, the topical composition comprises 0.02% to 15% by weight of the purified oil extract. In some embodiments, the topical composition comprises 0.02% to 10%, or 0.02% to 5% by weight of the purified oil extract. The amount or volume of the topical composition that is applied to the skin during the applying step can vary depending upon the particular concentration of purified oil extract included in the topical composition. In addition, the amount or volume of the topical composition applied to the skin during the applying step varies proportionally with the area of skin to be treated. In other words, when the area of skin being treated is relatively larger, a relatively larger volume of topical composition will be utilized in the method. In one embodiment, at least 0.001 to 0.1 grams of the purified oil extract is applied per $cm^2$ of treated skin. In some embodiments, 0.002 to 0.05 grams of the purified oil extract is applied per $cm^2$ of treated skin. In some embodiments, 0.005 to 0.05 grams of the purified oil extract is applied per $cm^2$ of treated skin.

The purified oil extract from *Melaleuca alternifolia* can be obtained by known methods that begin with removal of the oil from the natural product (such as by distillation, including steam distillation) and then continue on with a purification step that includes removal of a substantial portion (i.e., generally 80-99% and typically 90-99%) of the monoterpenes that are present in the distilled oil. Methods for obtaining the purified oil extract are described in U.S. Patent Application Publication Nos. 2006/0068044, 2008/0026083, which are specifically incorporated herein by reference. The purified oil extract that is useful in the methods disclosed herein (and in the compositions for use with those methods) includes 10% or less monoterpenes, 50% to 70% terpinen-4-ol and 8% to 30% sesquiterpenes. In one embodiment, the sesquiterpenes include 4% to 6.5% alpha-terpineol, 2% to 7% aromadendrene, 1.5% to 5% viridiflorene, and 1.5% to 3.5% delta cadinene. In one embodiment, the purified oil extract includes 0.5% to 2% globulol and 0.3% to 0.8% viridiflorol. An acceptable purified oil extract for use in the methods disclosed herein (and in the compositions for use with those methods) is commercially available as MK-ACTIVE™ (from Ad-Med Biotechnology, LLC) in both oil form and gelatin capsule form. The gelatin capsules contain 150 mg, 50 mg or 25 mg of purified oil extract. The oil form is 100% purified oil extract from *Melaleuca alternifolia*.

In certain embodiments, the topical composition may include one or more ingredients such as solvents, thickeners or gelling agents, coloring materials, fillers, pigments, antioxidants, preservatives, fragrances, electrolytes, neutralizing agents, film-forming polymers, UV blocking agents, skin conditioning agents, antidandruff agents, moisturizers, film formers, make-up agents, pharmaceuticals, emulsifiers, humectants, emollients, antiseptic agents, dermatologically acceptable carriers, surfactants, abrasives, absorbents, essential oils, skin sensates, astringents, antifoaming agents, antimicrobials, binders, biological additives, enzymes, enzyme inhibitors, enzyme activators, coenzymes, botanical extracts, ceramides, addition peptides, buffering agents, bulking agents, chelating agents, cosmetic biocides, denaturant drug astringents, external analgesics, polymers, substantivity increasing agents, opacifying agents, pH adjusters, propellants, reducing agents, sequestrants, skin bleaching agents, skin lightening agents, skin-conditioning agents, skin soothing agents, skin healing agents, aloe vera, pantothenic acid and derivatives thereof, allantoin, bisabolol, dipotassium glycyrrhizinate, skin treating agents, liposomes, naturally occurring stem cells obtained from either plants or mammals, penetrating enhancers (e.g., DMSO), vitamins, and combinations thereof. More specifically, various vitamins may be useful, including, but not limited to Vitamin A, Vitamin E and Vitamin C, available from Hoffmann-La Roche Ltd. As well, various botanical extracts may be useful, including, but not limited to green tea extract and ginseng extract, available from Mountain Rose Herbs of Eugene, Oreg. Various other additives, known to those of skill in the art, may be useful in the topical compositions, including, but not limited to vinegar and baking soda, which may be added to the topical composition to increase the cleaning action.

In certain embodiments, the topical composition may include one or more additional active ingredients. Active ingredients may include proteins, protein hydrolysates, amino acids, polyols, urea, allantoin, sugars and sugar derivatives, plant extracts, hydroxy acids, retinol or tocopherol derivatives, 5-(n-octanoyl)salicylic acid, esters of hydroxy acids, phospholipids, and combinations thereof. The topical composition may also include one or more additional non-active ingredients, including, but not limited to those described above. Preferred non-active ingredients include solvents, thickeners or gelling agents, coloring materials, fillers, pigments, antioxidants, preservatives, fragrances, electrolytes, neutralizing agents, polymers, UV blocking agents, and combinations thereof.

In one embodiment, the topical composition may include a hair growth stimulating agent (in addition to the purified oil extract), a hair density increasing agent, a hair lightening agent, and combinations thereof. Various hair growth stimulating agents, hair density increasing agents and hair lightening agents are well known to those of skill in the art. Hair growth stimulating agents and hair density increasing agents include, but are not limited to, prostaglandin A2, prostaglandin F2, prostaglandin E1, prostaglandin E2, Arbaprostil, Carboprost, Enprostil, Bimatoprost, Bemeprost, Latanaoprost, Limaprost, Minoxidil, Misoprostol, Ornoprostil, Prostacyclin, Prostaglandin E1, Prostaglandin E2, Prostaglandin F2.alpha., Rioprostil, Rosaprostol, Sulprostone, Travaprost, Trimoprostil, Viprostol, 15-PGDH inhibitors, and combinations thereof. Hair lightening agents include, but are not limited to, hydroquinone, citric acid, perborate or persulfate salts, kojic acid, ascorbic acid, hydrogen peroxide, urea peroxide, melamine peroxide, sodium perborate, sodium percarbonate, sodium persulfate, and combinations thereof.

An exemplary method for stimulating the growth of human hair may further include the application of a photosensitizer to the skin and the step of irradiating the skin area to which the photosensitizer has been applied with light containing a wavelength of about 400 to about 900 nm. Such methods are known to those of skill in the art and include the methods described in U.S. Patent Application Publication No. 20040015214 which is herein specifically incorporated by reference.

Preventing Hair Loss

An exemplary method for preventing human hair loss is provided. As used herein the term preventing human hair loss means maintaining or increasing the density of hair (i.e., the number of hairs per $cm^2$ of skin) that is growing in a given area of the human body as compared to the density of hair present in a similar area of the same person's body to which the method has not been applied. In certain embodiments, the density is maintained to within at least 95% (or more) of the original density when the method is utilized for at least 4 weeks, at least 6 weeks or at least 8 weeks. In some embodiments, the method results in the density being maintained to at least 90%, at least 80%, at least 70%, at least 60% or at least 50% within the same time period. In these embodiments, the density of the hair in the area to which the methods have been applied is relatively higher than the density of hair present in a similar area of the same person's body to which the method has not been applied, after the method has been utilized for at least 8 weeks, at least 14 weeks or at least 18 weeks. In some embodiments, the method results in the density being increased by at least 10% when the method is utilized for at least 8 weeks, at least 14 weeks or at least 18 weeks. In some embodiments, the method results in increases in density of at least 20%, at least 25%, at least 30%, at least 40%, at least 50% or more when utilized for the same time periods. The exemplary method includes providing a topical composition comprising 0.02% to 25% by weight of the purified oil extract from *Melaleuca alternifolia*. The exemplary method may further include applying the topical composition to the skin surrounding the follicles of the human hair at least once a day. In one embodiment, applying the topical composition occurs twice a day. In other embodiments, applying the topical composition occurs more frequently, such as three times a day, four times a day or more.

In one embodiment, the step of applying the topical composition to the skin is done carefully to ensure that the topical composition is substantially applied only to the skin and to avoid applying the topical composition to the hair (i.e., more than 95% of the topical composition is applied to the skin or less than 5% of the topical composition has contact with the outer 50% of the length of the hair strands). In some embodiments, the human hair being treated includes eyelashes and the step of applying the topical composition includes application of the topical composition to an area including an eyelid in the immediate vicinity of the normal lash line, eyelashes, and the base of the eyelash.

In one embodiment, application of the topical composition includes rubbing the topical composition into the skin. In some embodiments, the topical composition is rubbed into the skin for from a few seconds to half a minute. In other embodiments, the topical composition is rubbed into the skin from approximately half a minute to approximately one minute. In yet other embodiments, the topical composition is rubbed into the skin for longer than one minute, such as for two minutes. In some embodiments, the topical composition that has been applied to the skin may be allowed to remain on the skin for extended periods of time. In one embodiment, the topical composition may be allowed to remain on the skin after the application for one hour. In one embodiment, the topical composition may be allowed to remain on the skin after application for two hours. In one embodiment, the topical composition may be allowed to remain on the skin after application for four hours. In one embodiment, the topical composition may be allowed to remain on the skin indefinitely after the application. In this embodiment, the topical composition is not removed from the skin such as by wiping, washing or rinsing, but is instead allowed to remain on the skin until it is removed by normal or routine hygiene practices such as shampooing or washing. In certain embodiments, after the topical composition is applied to the skin, heat is applied to the skin such as from a hair dryer or heating pad to aid in absorption of the composition.

In one embodiment, the exemplary method for preventing human hair loss is also effective in bringing back the natural pigmentation of hair. A method is effective in bringing back the natural pigmentation of hair if its usage results in at least 15% of re-growing hair strands growing from the skin to which the composition has been applied having pigmentation (as opposed to lacking pigmentation e.g., by being clear to gray). In other embodiments, relatively more of the hair strands have a return of pigmentation (e.g., 20% or more, 25% or more, or even 50% or more). Preferably, this occurs after the method is utilized for at least 8 weeks, and in some instances at least 14 weeks or at least 18 weeks.

For convenience or efficacy of application, the topical composition may be provided in various forms including, but not limited to, application stick, mascara, eyebrow coloring, lotions, creams, aerosols, sprays, gels, foams, ointments, oils, mousse, emulsions, colloidals, solutions, suspensions, spray-on formulations, brush-on formulations, hair spray, moisturizer, and combinations thereof.

The topical composition may comprise at least 0.02% by weight of the purified oil extract. In one embodiment, the topical composition comprises 0.02% to 25% by weight of the purified oil extract. In some embodiments, the topical composition comprises 0.02% to 15% by weight of the purified oil extract. In some embodiments, the topical composition comprises 0.02% to 10% or 0.02% to 5% by weight of the purified oil extract. The amount or volume of the topical composition that is applied to the skin during the applying step can vary depending upon the particular concentration of purified oil extract included in the topical composition. In addition, the amount or volume of the topical composition applied to the skin during the applying step varies proportionally with the area of skin to be treated. In other words, when the area of skin being treated is relatively larger, a relatively larger volume of topical composition will be utilized in the method. In one embodiment, at least 0.001 to 0.1 grams of the purified oil extract is applied per $cm^2$ of treated skin. In some embodiments, 0.002 to 0.05 grams of the purified oil extract is applied per $cm^2$ of treated skin. In some embodiments, 0.005 to 0.05 grams of the purified oil extract is applied per $cm^2$ of treated skin.

The purified oil extract from *Melaleuca alternifolia* can be obtained by known methods that begin with removal of the oil from the natural product (such as by distillation, including steam distillation) and then continue on with a purification step that includes removal of a substantial portion (i.e., generally 80-99% and typically 90-99%) of the monoterpenes that are present in the distilled oil. Methods for obtaining the purified oil extract are described in U.S. Patent Application Publication Nos. 2006/0068044, 2008/0026083, which are specifically incorporated herein by reference. The purified oil extract that is useful in the methods disclosed herein (and in the compositions for use with those methods) includes 10% or less monoterpenes, 50% to 70% terpinen-4-ol and 8% to 30% sesquiterpenes. In one embodiment, the sesquiterpenes include 4% to 6.5% alpha-terpineol, 2% to 7% aromadendrene, 1.5% to 5% viridiflorene, and 1.5% to 3.5% delta cadinene. In one embodiment, the purified oil extract includes 0.5% to 2% globulol and 0.3% to 0.8% viridiflorol. An acceptable purified oil extract for use in the methods disclosed herein (and in the compositions for use with those methods) is commercially available as MK-ACTIVE™ (from Ad-Med Biotechnology, LLC) in gelatin capsule form. The gelatin capsules contain 150 mg, 50 mg or 25 mg of purified oil extract.

In certain embodiments, the topical composition may include one or more ingredients such as solvents, thickeners or gelling agents, coloring materials, fillers, pigments, antioxidants, preservatives, fragrances, electrolytes, neutralizing agents, film-forming polymers, UV blocking agents, skin conditioning agents, antidandruff agents, moisturizers, film formers, make-up agents, pharmaceuticals, emulsifiers, humectants, emollients, antiseptic agents, dermatologically acceptable carriers, surfactants, abrasives, absorbents, essential oils, skin sensates, astringents, antifoaming agents, antimicrobials, binders, biological additives, enzymes, enzyme inhibitors, enzyme activators, coenzymes, botanical extracts, ceramides, addition peptides, buffering agents, bulking agents, chelating agents, cosmetic biocides, denaturant drug astringents, external analgesics, polymers, substantivity increasing agents, opacifying agents, pH adjusters, propellants, reducing agents, sequestrants, skin bleaching agents, skin lightening agents, skin-conditioning agents, skin soothing agents, skin healing agents, aloe vera, pantothenic acids and derivatives thereof, allantoin, bisabolol, dipotassium glycyrrhizinate, skin treating agents, liposomes, naturally occurring stem cells obtained from either plants or mammals, penetrating enhancers (e.g., DMSO), vitamins, and combinations thereof. More specifically, various vitamins may be useful, including, but not limited to Vitamin A, Vitamin E and Vitamin C, available from Hoffmann-La Roche Ltd. As well, various botanical extracts may be useful, including, but not limited to green tea extract and ginseng extract, available from Mountain Rose Herbs in Eugene, Oreg. Various other additives, known to those of skill in the art, may be useful in the topical compositions, including, but not limited to vinegar and baking soda, which may be useful to increase the cleaning action of the topical composition.

In certain embodiments, the topical composition may include one or more additional active ingredients. Active ingredients may include proteins, protein hydrolysates, amino acids, polyols, urea, allantoin, sugars and sugar derivatives, plant extracts, hydroxy acids, retinol or tocopherol derivatives, 5-(n-octanoyl)salicylic acid, esters of hydroxy acids, phospholipids, and combinations thereof. The topical composition may also include one or more additional non-active ingredients, including, but not limited to those described above. Preferred non-active ingredients include solvents, thickeners or gelling agents, coloring materials, fillers, pigments, antioxidants, preservatives, fragrances, electrolytes, neutralizing agents, polymers, UV blocking agents, and combinations thereof.

In one embodiment, the topical composition may include a hair growth stimulating agent (in addition to the purified oil extract), a hair density increasing agent, a hair lightening agent, and combinations thereof. Various hair growth stimulating agents, hair density increasing agents and hair lightening agents are well known to those of skill in the art. Hair growth stimulating agents and hair density increasing agents, include, but are not limited to prostaglandin A2, prostaglandin F2, prostaglandin E1, prostaglandin E2, Arbaprostil, Carboprost, Enprostil, Bimatoprost, Bemeprost, Latanaoprost, Limaprost, Minoxidil, Misoprostol, Ornoprostil, Prostacyclin, Prostaglandin E1, Prostaglandin E2, Prostaglandin F2.alpha., Rioprostil, Rosaprostol, Sulprostone, Travaprost, Trimoprostil, Viprostol, 15-PGDH inhibitors, and combinations thereof. Hair lightening agents include, but are not limited to, hydroquinone, citric acid, perborate or persulfate salts, kojic acid, ascorbic acid, hydrogen peroxide, urea peroxide, melamine peroxide, sodium perborate, sodium percarbonate, sodium persulfate, and combinations thereof.

An exemplary method for preventing human hair loss may further include the application of a photosensitizer to the skin and the step of irradiating the skin area to which the photosensitizer has been applied with light containing a wavelength of about 400 to about 900 nm. Such methods are known to those of skill in the art and include the methods described in U.S. Patent Application Publication No. 20040015214 which is herein specifically incorporated by reference.

Example 1

FIGS. 1-4 are photographs of Scanning Electron Microscope (SEM) images showing individual human hairs at various magnifications. The photographs are all of the same hair strand, but each photograph focuses on a different point along the length of the hair strand in order to show changes to the hair that occurred as the individual utilized the treatment methods and topical compositions disclosed herein. In EXAMPLE 1, the hair was treated by applying 3 to 5 sprays of a topical composition including 80% water, 18% denatured grain alcohol, 0.95% purified tea tree oil extract, 0.005% white vinegar, 1% glycerin, 0.005% vitamin E, 0.005% vitamin C, 0.005% vitamin E, 0.005% panthenol, 0.005% calendula flower, 0.005% Green Tea, 0.005% Ginseng, 0.005% Nettle, and 0.005% baking soda on thinning and balding areas of a scalp in the morning. The topical composition is then massaged into the scalp for about five seconds. The treatment was repeated in the evening.

Figure 1:
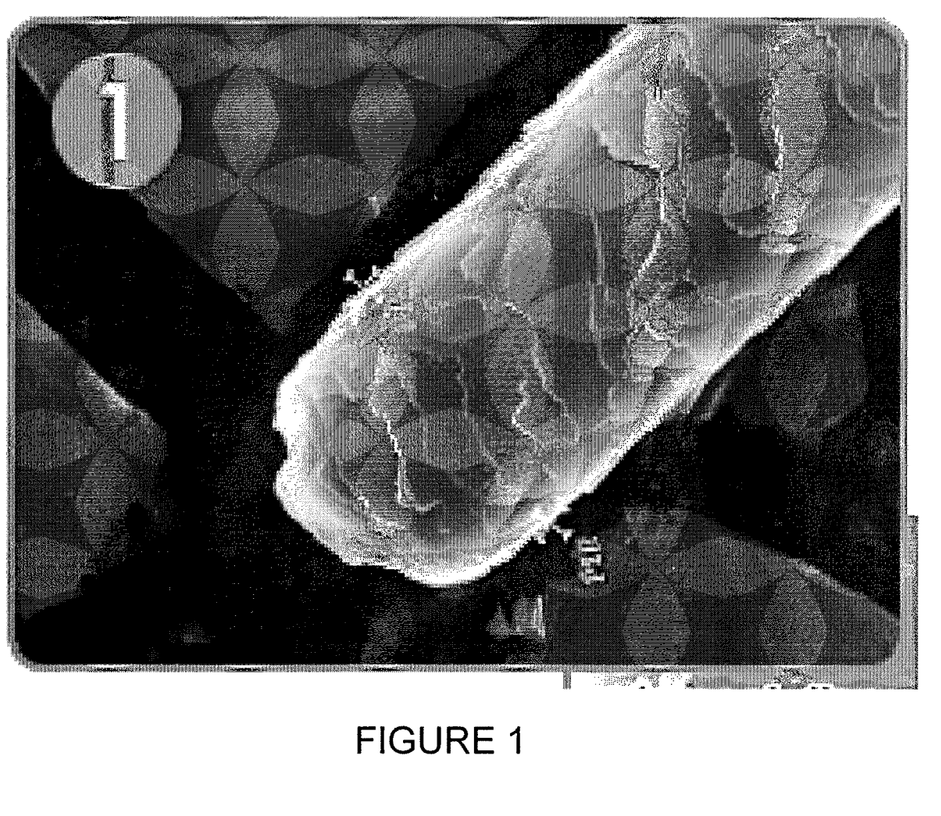
FIG. 1 is a photograph of a strand of hair under a Scanning Electron Microscope at 1000× magnification.
Figure 2:
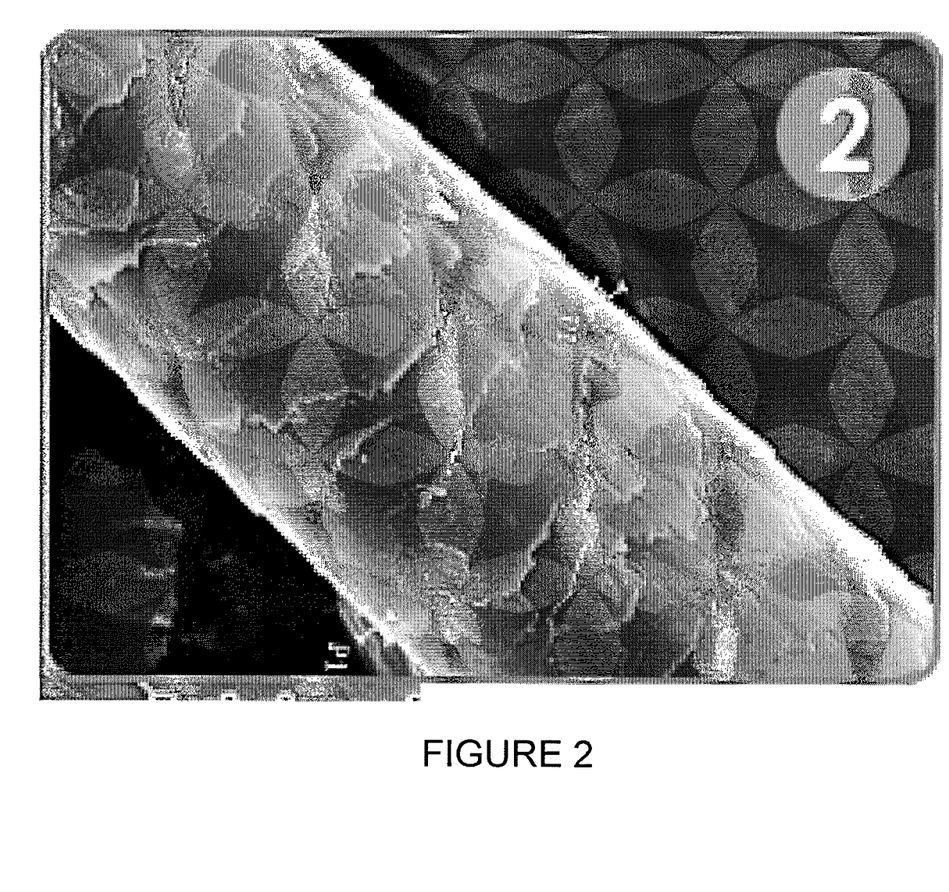
FIG. 2 is a photograph of a strand of hair under a Scanning Electron Microscope at 1000× magnification.
Figure 3:
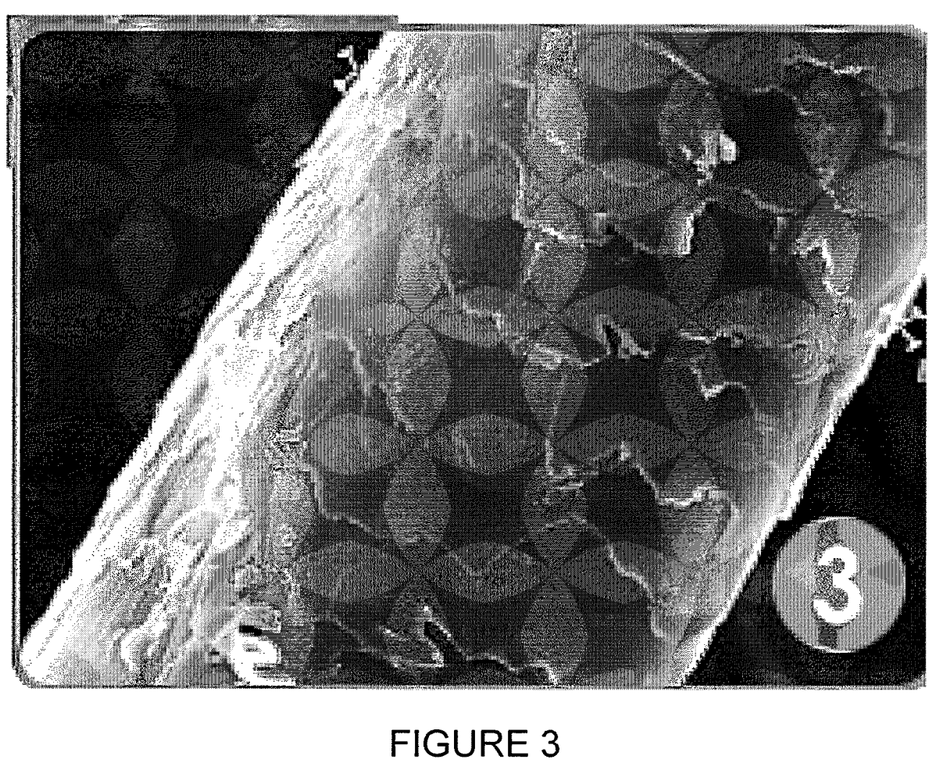
FIG. 3 is a photograph of a strand of hair under a Scanning Electron Microscope at 1000× magnification.

FIG. 1 is a photograph of the tip or end of the hair at 1000× magnification, indicating the condition of the hair before that individual began a regimen that included use of the treatment methods and topical compositions disclosed herein. From the photograph it can be seen that the tip of the hair is relatively thin and weak with no pigmentation. FIG. 2 is a photograph showing a different location along the length of the same hair strand, at 1000× magnification, indicating the condition of the hair after the individual had been using the regimen that included the above described treatment and topical compositions for approximately eight weeks. From the photograph it can be seen that the hair is increasing in size (thickness/diameter), strength and gaining pigmentation. FIG. 3 is a photograph showing yet another location along the length of the same hair strand, at 1000× magnification, indicating the condition of the hair after the individual had been continuing with the same regimen for a total of about three months. From the photograph, it can be seen that the hair is continuing to increase in thickness/diameter and is stronger.

Figure 4:
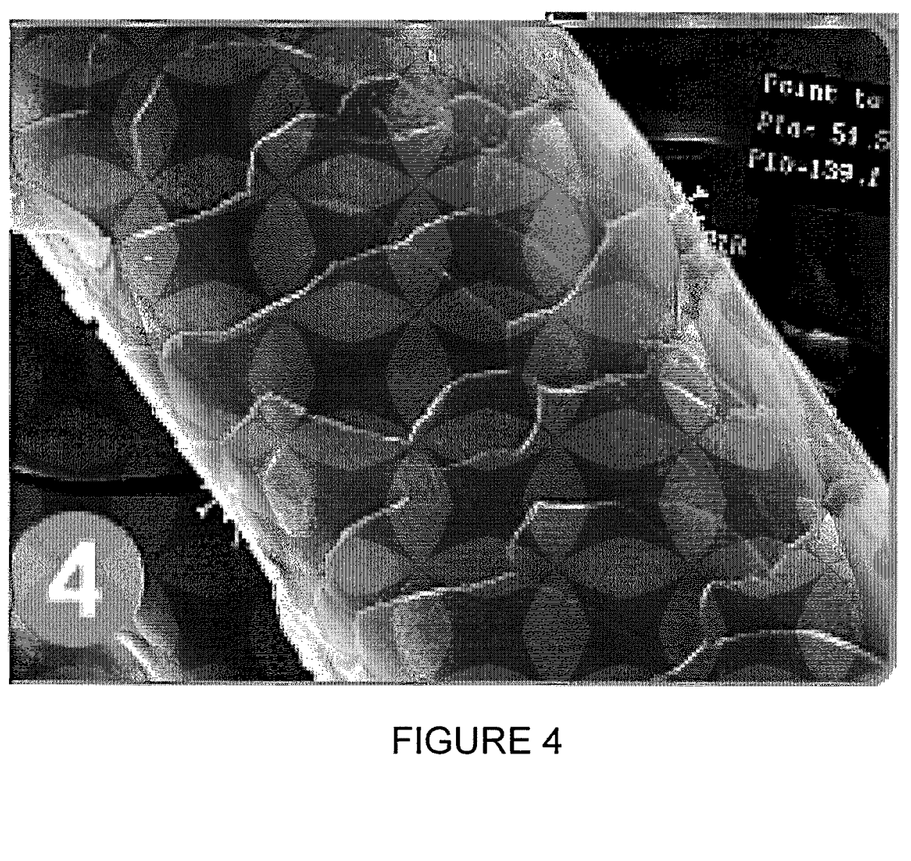
FIG. 4 is a photograph of a strand of hair under a Scanning Electron Microscope at 1000× magnification.

FIG. 4 is a photograph showing yet another location along the length of the same hair strands, at 1000× magnification, indicating the condition of the hair after the individual had been continuing with the same regimen for a total of approximately four months. From the photograph, it can be seen that the hair is continuing to increase in thickness (now having a diameter that is almost double that in photograph 1(a). Without being bound to any theory, it is believed that on the untreated scalp, the hair follicle had been choked by sebum, dead skin and an over production of flora (e.g., bacteria) which will slowly suffocate the hair follicle and reduce the size of the hair and slow the overall growth of the hair. If untreated, the hair will begin to suffocate leaving a think, weak non-pigmented hair in a dormant state.

Example 2

Figure 5:
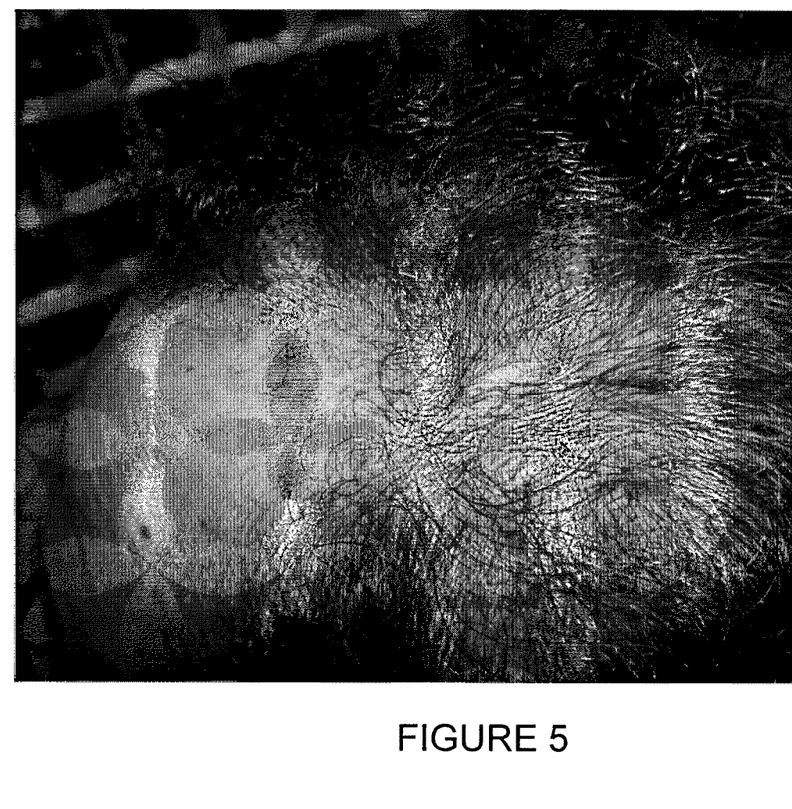
FIG. 5 is a photograph of a scalp before it is treated with a topical composition.
Figure 6:
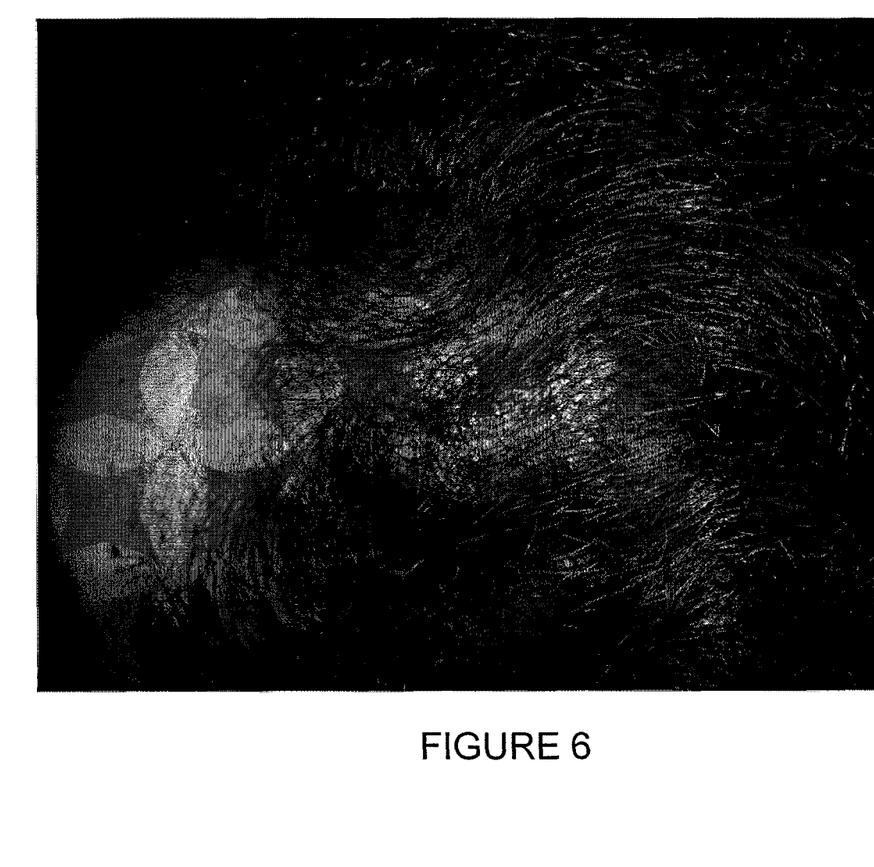
FIG. 6 is a photograph of the scalp of FIG. 5, eight weeks after it was treated with a topical composition.

FIGS. 5 and 6 are before and after photographs of a female individual. FIG. 5 is a photograph of the individual's scalp before that individual began a regimen that included use of the methods and topical compositions disclosed herein. In this example, the individual applied four sprays of the topical composition described in EXAMPLE 1 twice a day, once in the morning and once at night. After each application the topical composition was rubbed into the individual's scalp and allowed to dry. FIG. 6 is a photograph of the same individual's scalp after a period of eight weeks. As shown in FIG. 6, the hair became thicker and new hair started to grow where there was no hair before.

Example 3

Figure 7:
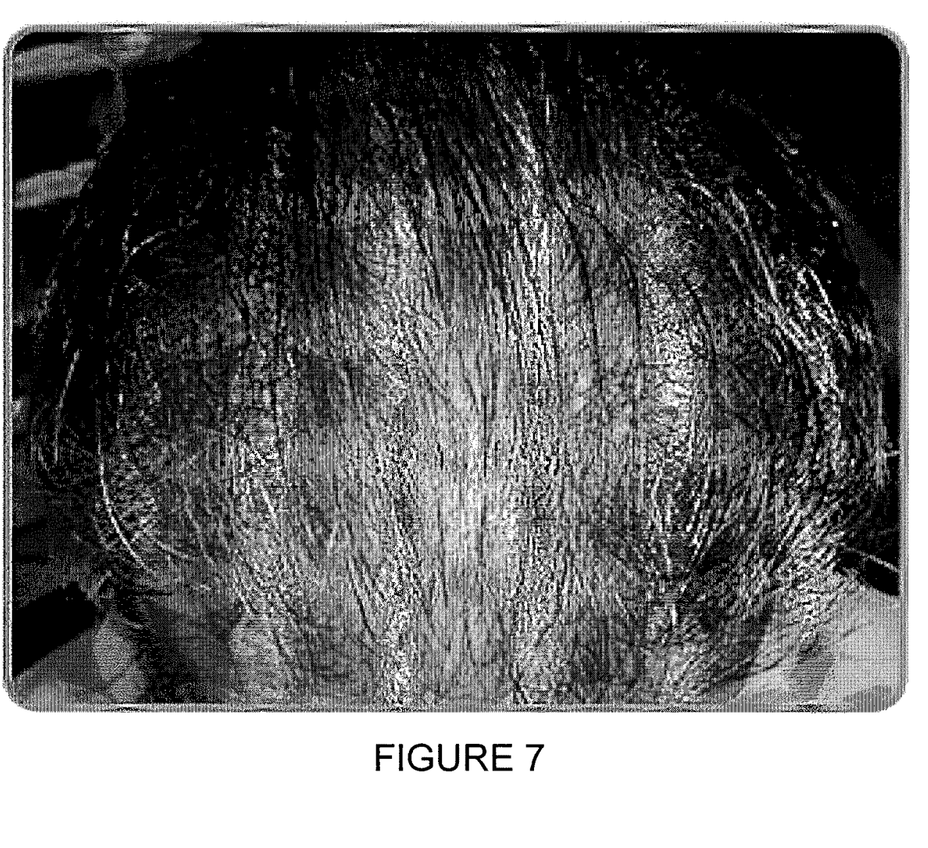
FIG. 7 is a photograph of a scalp before it is treated with a topical composition.
Figure 8:
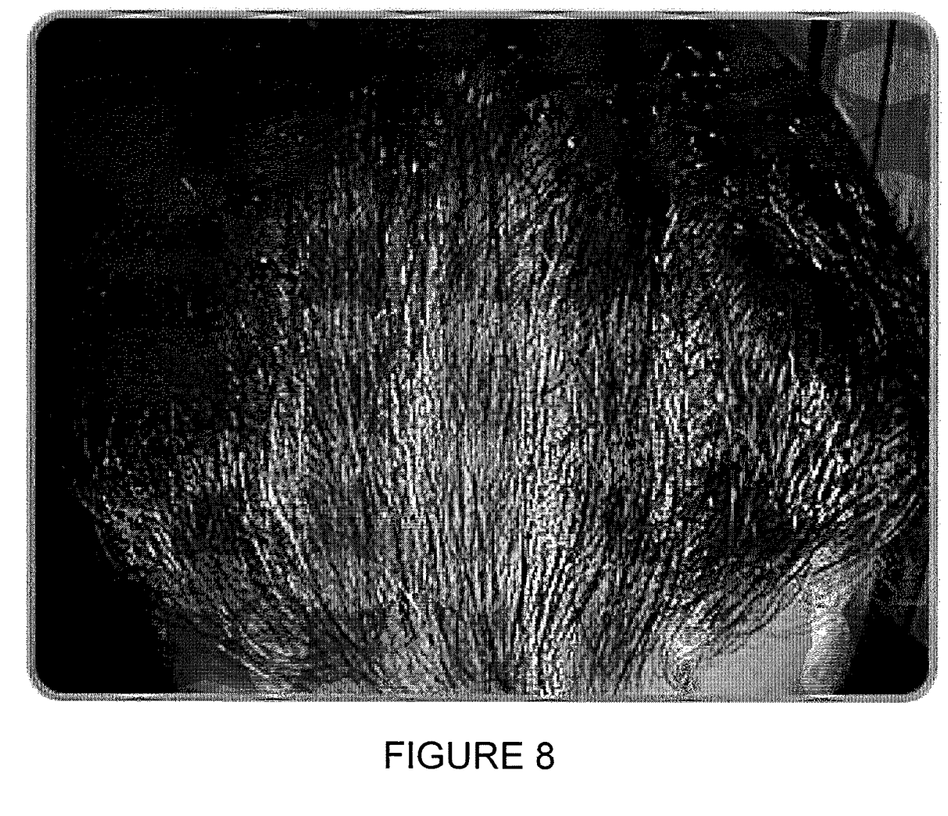
FIG. 8 is a photograph of the scalp of FIG. 7, twelve weeks after it was treated with a topical composition.

FIGS. 7 and 8 are before and after photographs of a male individual. FIG. 7 is a photograph of the individual's scalp before that individual began a regimen that included use of the methods and topical compositions disclosed herein. In this example, the individual applied four sprays of the topical composition described in EXAMPLE 1 twice a day, once in the morning and once at night. After each application the topical composition was rubbed into the individual's scalp and allowed to dry. FIG. 8 is a photograph of the same individual's scalp after a period of twelve weeks. As shown in FIG. 8, the hair on the crown area of the individual's head is thicker and there is new growth.

Example 4

Figure 9:
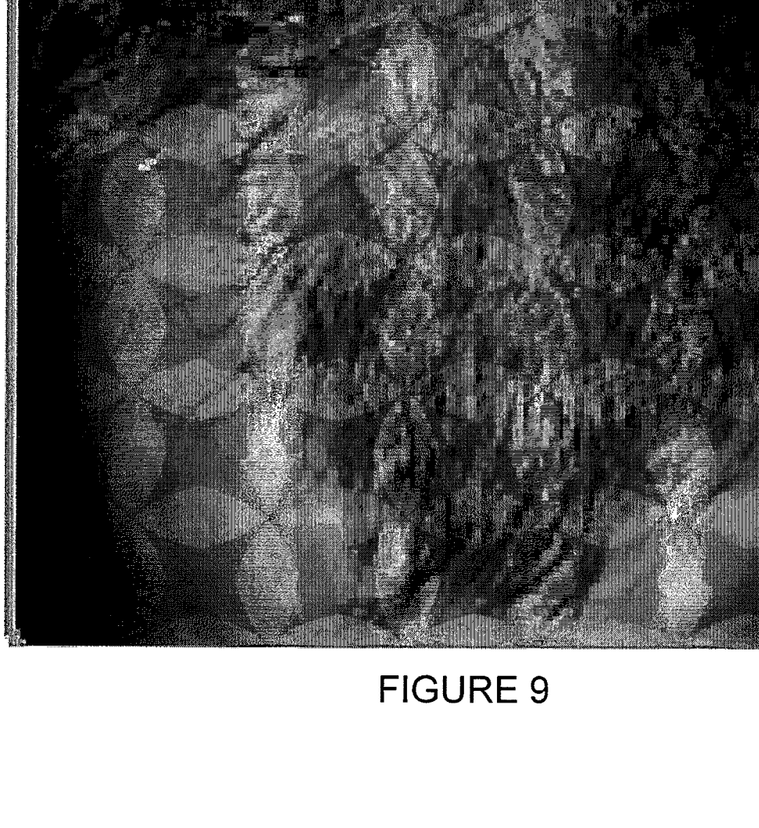
FIG. 9 is a photograph of a scalp before it is treated with a topical composition.
Figure 10:
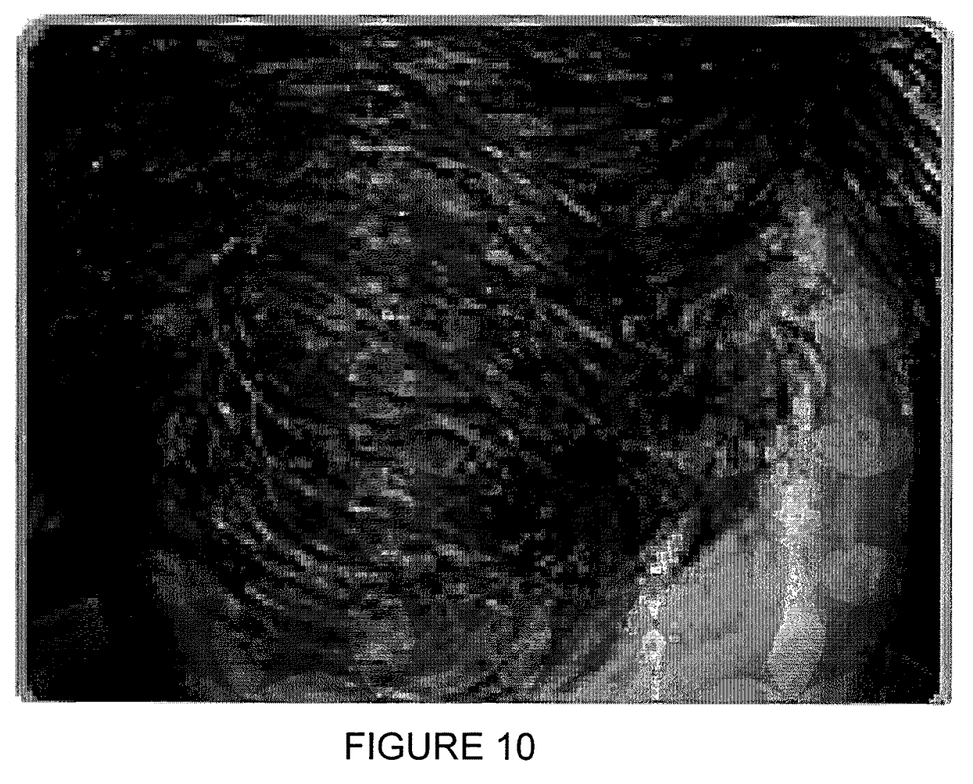
FIG. 10 is a photograph of the scalp of FIG. 9, ten weeks after it was treated with a topical composition.

FIGS. 9 and 10 are before and after photographs of an individual. FIG. 9 is a photograph of the individual's scalp before that individual began a regimen that included use of the methods and topical compositions disclosed herein. In this example, the individual applied five sprays of the topical composition described in EXAMPLE 1 twice a day, once in the morning and once at night. After each application the topical composition was rubbed into the individual's scalp and allowed to dry. FIG. 10 is a photograph of the same individual's scalp after a period of ten weeks. As shown in FIG. 10, the hair increased in thickness and new hair has begun to fill in the front area of the scalp.

Exemplary Topical Compositions and Methods of Use

Formulation 1

Various topical compositions were formulated according to the formulas provided below in Table 1.

TABLE 1

|  | wt. % | wt % | wt % |
|---|---|---|---|
| Purified oil extract[1] | 1.0 | 2.0 | 5.0 |

TABLE 1-continued

|  | wt. % | wt % | wt % |
|---|---|---|---|
| Alcohol SDA | 18.0 | 18.0 | 18.0 |
| Glycerin | 1.0 | 1.0 | 1.0 |
| Water | 80.0 | 79.0 | 76.0 |

[1]MK-ACTIVE ™ oil

The ingredients were mixed according to the following procedure. First the alcohol was added to a suitable container. Then, with moderate mixing the purified oil extract was added and mixed for about 5 minutes. Next, glycerin was added and mixing was continued for about another 5 minutes. Finally, water was added with moderate mixing. The resulting product began somewhat cloudy upon addition and mixing of the water.

The first composition (containing 1.0 wt % purified oil extract) was then placed into a standard spray bottle that dispensed approximately 0.18 grams of topical composition per spray. The topical composition was applied to the scalp twice a day, in the morning and at night using the spray bottle, and with 4-6 sprays per application (varying depending upon the area of application). The spray was directed to areas of the scalp where hair was thinning or missing.

Within 6 weeks, the growth of small hairs was noticeable on areas of the scalp where hair was previously missing or thinning After 12 weeks, the new hairs were thicker and pigmentation was appears at the root of the hair. After 6 months of application of the topical composition, according to the above method, the new hairs were even thicker and darker and the overall effect was that the head hair appeared thicker and darker.

Formulations 2 and 3

Various topical compositions were formulated according to the formulas provided below in Table 2.

|  | Formulation 2 wt. % | Formulation 3 wt % |
|---|---|---|
| Purified oil extract[1] | 1 | 2 |
| Alcohol SDA | 18.0 | 18.0 |
| Glycerin | 1.0 | 1.0 |
| Water | 78.5 | 77.1 |
| Green Tea Extract[2] | 0.1 | 0.1 |
| Ginseng Extract[3] | 0.1 | 0.1 |
| White Vinegar[4] | 0.5 | 0.7 |
| Baking Soda | 0.5 | 0.7 |
| Vitamin A[5] | 0.1 | 0.1 |
| Vitamin E[6] | 0.1 | 0.1 |
| Vitamin C[7] | 0.1 | 0.1 |

[1]MK-ACTIVE ™ oil
[2]Green Tea Extracts, Mountain Rose Herbs
[3]Ginseng Extract, Mountain Rose Herbs
[4]White Vinegar, Heinz Inc.
[5]Hoffman LaRoche Ltd.
[6]Hoffman LaRoche Ltd.
[7]Hoffman LaRoche Ltd.

In Formulations 2 and 3, the ingredients were mixed according to the following procedure. First the alcohol was added to a suitable container. Then, with moderate mixing the purified oil extract was added and mixed for about 5 minutes. Next, glycerin was added and mixing was continued for about another 5 minutes. The remaining components were also added to the container and mixed for another 5 minutes. Finally, water was added with moderate mixing. The resulting product began somewhat cloudy upon addition and mixing of the water.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A method for stimulating the growth of human hair comprising:
   providing a topical composition comprising an active ingredient of 0.02% to 25% by weight of a purified oil extract from Melaleuca alternifolia;
   applying the composition to the skin surrounding the follicles of the human hair at least once a day for at least 8 weeks; and
   wherein the purified oil extract comprises 10% or less monoterpenes, 50% to 70% terpinen-4-ol and 8% to 30% sesquiterpenes and wherein the method is effective in increasing the density of human hair by at least 10%, where density is measured by the number of human hairs in a given area of skin.

2. The method of claim 1 wherein the topical composition comprises 0.02% to 15% by weight of the purified oil extract.

3. The method of claim 1 wherein the topical composition comprises 0.02% to 10% by weight of the purified oil extract.

4. The method of any of claim 1 wherein the topical composition is rubbed into the skin.

5. The method of claim 4 where the topical composition that has been rubbed into the skin is allowed to remain on the skin in that it is not removed such as by wiping, washing or rinsing.

6. The method of any of claim 1 wherein the sesquiterpenes comprise 4% to 6.5% alpha-terpineol, 2% to 7% aromadendrene, 1.5% to 5% viridiflorene, and 1.5% to 3.5% delta cadinene.

7. The method of claim 1 wherein the purified oil extract further comprises 0.5% to 2% globulol and 0.3% to 0.8% viridiflorol.

8. The method of claim 1 wherein the topical composition further comprises at least one ingredient selected from the group consisting of solvents, thickeners or gelling agents, coloring materials, fillers, pigments, antioxidants, preservatives, fragrances, electrolytes, neutralizing agents, film-forming polymers, UV blocking agents, skin conditioning agents, antidandruff agents, moisturizers, film formers, make-up agents, pharmaceuticals, emulsifiers, humectants, emollients, antiseptic agents, dermatologically acceptable carriers, surfactants, abrasives, absorbents, essential oils, skin sensates, astringents, antifoaming agents, antimicrobials, binders, biological additives, enzymes, enzyme inhibitors, enzyme activators, coenzymes, botanical extracts, ceramides, addition peptides, buffering agents, bulking agents, chelating agents, cosmetic biocides, denaturant drug astringents, external analgesics, polymers, substantivity increasing agents, opacifying agents, pH adjusters, propellants, reducing agents, sequestrants, skin bleaching agents, skin lightening agents, skin-conditioning agents, skin soothing agents, skin healing agents, aloe vera, pantothenic acid, allantoin, bisabolol, dipotassium glycyrrhizinate, skin treating agents, liposomes, stem cells, penetrating enhancers, DMSO, vitamins, and combinations thereof.

9. The method of claim 1 wherein the topical composition further comprises at least one additional active ingredient selected from the group consisting of proteins, protein hydrolysates, amino acids, polyols, urea, allantoin, sugars, plant extracts, hydroxy acids, retinol or tocopherol, 5-(n-octanoyl)salicylic acid, esters of hydroxy acids, phospholipids, and combinations thereof.

10. The method of claim 1 wherein the hair is selected from the group consisting of head hair, scalp hair, eyelashes, eyebrows, mustaches, beards, chest hair, leg hair, arm hair, and combinations thereof.

11. The method of claim 1 wherein the topical composition further comprises at least one of a hair growth stimulating agent, a hair density increasing agent, and a hair lightening agent.

12. The method of claim 11 wherein the hair growth stimulating agent is selected from the group consisting of prostaglandin A2, prostaglandin F2, prostaglandin E1, prostaglandin E2, arbaprostil, carboprost, enprostil, bimatoprost, bemeprost, latanaoprost, limaprost, minoxidil, misoprostol, ornoprostil, prostacyclin, prostaglandin E1, prostaglandin E2, prostaglandin F2.alpha., rioprostil, rosaprostol, sulprostone, travaprost, trimoprostil, viprostol, 15-PGDH inhibitors, and combinations thereof.

13. The method of claim 1 wherein the topical composition is in a form selected from the group consisting of application stick, mascara, eyebrow coloring, lotions, creams, sprays, gels, foams, ointments, oils, mousse, emulsions, colloidals, solutions, suspensions, spray-on formulations, brush-on formulations, hair spray, moisturizer, and combinations thereof.

14. The method of claim 1 wherein the topical composition is in a form selected from the group consisting of aerosols, sprays, creams, ointments, gels and oils.

15. The method of claim 1 further comprising at least one inactive ingredient selected from the group consisting of solvents, thickeners or gelling agents, coloring materials, fillers, pigments, antioxidants, preservatives, fragrances, electrolytes, neutralizing agents, polymers, UV blocking agents, and combinations thereof.

16. The method of claim 1 where the step of applying the composition occurs twice a day.

17. The method of claim 1 wherein the composition is also effective in bringing back the natural pigmentation of the hair.

18. The method of claim 1 wherein the method is for treating hair loss resulting from alopecia and the step of applying the topical composition consists of application to the scalp at areas of thinning or complete hair loss.

19. The method of claim 1 wherein the human is a female.

20. The method of claim 1 wherein the human hair is eyelashes and the step of applying the composition includes application to at least one area selected from the group consisting of an eyelid in the immediate vicinity of the normal lash line, eyelashes, and the base of the eyelash.

21. The method of claim 1 further comprising the application of a photosensitizer to the skin and the step of irradiating the skin area to which the photosensitizer has been applied with light containing a wavelength of about 400 to about 900 nm.

22. A method for stimulating the growth of human hair comprising:
  providing a topical composition comprising an active ingredient of 0.02% to 25% by weight of a purified oil extract from *Melaleuca alternifolia;*
  applying the composition to the skin surrounding the follicles of the human hair at least once a day for at least 8 weeks; and
  wherein the purified oil extract comprises 10% or less monoterpenes, 50% to 70% terpinen-4-ol and 8% to 30% sesquiterpenes, 0.5% to 2% globulol and 0.3% to 0.8% viridiflorol,
  wherein the sesquiterpenes comprise 4% to 6.5% alpha-terpineol, 2% to 7% aromadendrene, 1.5% to 5% viridiflorene, and 1.5% to 3.5% delta cadinene and wherein the method is effective in increasing the density of the human hair by at least 10%, where density is measured by the number of human hairs in a given area of skin.

23. The method of claim 22 wherein the topical composition comprises 0.02% to 15% by weight of the purified oil extract.

24. The method of claim 22 wherein the topical composition comprises 0.02% to 10% by weight of the purified oil extract.

25. The method of claim 22 wherein the topical composition is rubbed into the skin.

26. The method of claim 22 where the topical composition that has been rubbed into the skin is allowed to remain on the skin in that it is not removed such as by wiping, washing or rinsing.

27. The method of claim 22 wherein the topical composition further comprises at least one ingredient selected from the group consisting of solvents, thickeners or gelling agents, coloring materials, fillers, pigments, antioxidants, preservatives, fragrances, electrolytes, neutralizing agents, film-forming polymers, UV blocking agents, skin conditioning agents, antidandruff agents, moisturizers, film formers, make-up agents, pharmaceuticals, emulsifiers, humectants, emollients, antiseptic agents, dermatologically acceptable carriers, surfactants, abrasives, absorbents, essential oils, skin sensates, astringents, antifoaming agents, antimicrobials, binders, biological additives, enzymes, enzyme inhibitors, enzyme activators, coenzymes, botanical extracts, ceramides, addition peptides, buffering agents, bulking agents, chelating agents, cosmetic biocides, denaturant drug astringents, external analgesics, polymers, substantivity increasing agents, opacifying agents, pH adjusters, propellants, reducing agents, sequestrants, skin bleaching agents, skin lightening agents, skin-conditioning agents, skin soothing agents, skin healing agents, aloe vera, pantothenic acid, allantoin, bisabolol, dipotassium glycyrrhizinate, skin treating agents, liposomes, stems cells, penetrating enhancers, DMSO, vitamins, and combinations thereof.

28. The method of claim 22 wherein the topical composition further comprises at least one additional active ingredient selected from the group consisting of proteins, protein hydrolysates, amino acids, polyols, urea, allantoin, sugars, plant extracts, hydroxy acids, retinol or tocopherol, 5-(n-octanoyl)salicylic acid, esters of hydroxy acids, phospholipids, and combinations thereof.

29. The method of claim 22 wherein the hair is selected from the group consisting of head hair, scalp hair, eyelashes, eyebrows, mustaches, beards, chest hair, leg hair, arm hair, and combinations thereof.

30. The method of claim 22 wherein the topical composition further comprises at least one of a hair growth stimulating agent, a hair density increasing agent, and a hair lightening agent.

31. The method of claim 30 wherein the hair growth stimulating agent is selected from the group consisting of prostaglandin A2, prostaglandin F2, prostaglandin E1, prostaglandin E2, arbaprostil, carboprost, enprostil, bimatoprost, bemeprost, latanaoprost, limaprost, minoxidil, misoprostol, ornoprostil, prostacyclin, prostaglandin E1, prostaglandin E2, prostaglandin F2.alpha., rioprostil, rosaprostol, sulprostone, travaprost, trimoprostil, viprostol, 15-PGDH inhibitors, and combinations thereof.

32. The method of claim 22 wherein the topical composition is in a form selected from the group consisting of application stick, mascara, eyebrow coloring, lotions, creams, sprays, gels, foams, ointments, oils, mousse, emulsions, colloidals, solutions, suspensions, spray-on formulations, brush-on formulations, hair spray, moisturizer, and combinations thereof.

33. The method of claim 22 wherein the topical composition is in a form selected from the group consisting of aerosols, sprays, creams, ointments, gels and oils.

34. The method of claim 22 further comprising at least one inactive ingredient selected from the group consisting of solvents, thickeners or gelling agents, coloring materials, fillers, pigments, antioxidants, preservatives, fragrances, electrolytes, neutralizing agents, polymers, UV blocking agents, and combinations thereof.

35. The method of claim 22 where the step of applying the composition occurs twice a day.

36. The method of claim 22 wherein the composition is also effective in bringing back the natural pigmentation of the hair.

37. The method of claim 22 wherein the method is for treating hair loss resulting from alopecia and the step of applying the topical composition consists of application to the scalp at areas of thinning or complete hair loss.

38. The method of claim 22 wherein the human is a female.

* * * * *